US009955755B2

(12) United States Patent
Heid

(10) Patent No.: US 9,955,755 B2
(45) Date of Patent: May 1, 2018

(54) THERAPEUTIC FOOTWEAR

(71) Applicant: Chele Suzanne Heid, Greenwood, IN (US)

(72) Inventor: Chele Suzanne Heid, Greenwood, IN (US)

(*) Notice: Subject to any disclaimer, the term of this patent is extended or adjusted under 35 U.S.C. 154(b) by 0 days. days.

(21) Appl. No.: 14/865,208

(22) Filed: Sep. 25, 2015

(65) Prior Publication Data

US 2016/0242508 A1 Aug. 25, 2016

Related U.S. Application Data

(63) Continuation of application No. 14/485,949, filed on Sep. 15, 2014, now Pat. No. 9,173,449, which is a continuation of application No. 13/079,009, filed on Apr. 3, 2011, now Pat. No. 8,832,971, which is a continuation-in-part of application No. 11/935,380, filed on Nov. 5, 2007, now abandoned.

(51) Int. Cl.
| | |
|---|---|
| *A43B 3/12* | (2006.01) |
| *A43C 11/14* | (2006.01) |
| *A43B 1/00* | (2006.01) |
| *A43B 7/26* | (2006.01) |
| *A61F 5/01* | (2006.01) |
| *A43B 7/14* | (2006.01) |
| *A43B 7/20* | (2006.01) |

(52) U.S. Cl.
CPC ............ *A43C 11/14* (2013.01); *A43B 1/0081* (2013.01); *A43B 3/122* (2013.01); *A43B 3/126* (2013.01); *A43B 7/14* (2013.01); *A43B 7/20* (2013.01); *A43B 7/26* (2013.01); *A43C 11/1493* (2013.01); *A61F 5/019* (2013.01)

(58) Field of Classification Search
CPC ........... A43B 3/126; A43B 3/122; A43B 7/26; A43B 1/0081; A43C 11/1493; A61F 5/019
USPC ..................................................... 36/94, 11.5
See application file for complete search history.

(56) References Cited

U.S. PATENT DOCUMENTS

| | | | |
|---|---|---|---|
| 1,402,375 A * | 1/1922 | Parisi ............................. 602/30 |
| 1,867,679 A * | 7/1932 | Riehle et al. ................... 602/30 |
| 2,506,308 A | 5/1950 | Maynier | |
| 2,734,285 A | 2/1956 | Levitt | |
| 2,751,693 A | 6/1956 | Baker | |
| 2,808,662 A | 10/1957 | Webb | |
| 3,066,678 A | 12/1962 | Riecken | |
| 3,275,002 A | 9/1966 | Scholl | |
| 3,987,559 A | 10/1976 | Roberts | |
| 4,207,880 A | 6/1980 | Zinkovich | |
| 4,393,876 A | 7/1983 | Dieterich | |
| 4,563,787 A | 1/1986 | Drew | |
| 4,583,303 A | 4/1986 | Laiacona et al. | |
| 4,632,103 A | 12/1986 | Fabricant et al. | |

(Continued)

*Primary Examiner* — Ted Kavanaugh
(74) *Attorney, Agent, or Firm* — Faegre Baker Daniels LLP

(57) ABSTRACT

The present invention generally relates to therapeutic footwear such as sandals, conventional shoes, and corrective inserts that may be inserted into conventional shoes. Specifically, the therapeutic footwear may be used for maintaining, correcting, or repositioning the great toe to decrease pressure on the first metatarsal-phalangeal joint or bunion. Additional therapeutic features may include spreading of the wearer's toes, supporting the wearer's arch to control excessive pronation, and providing sustained heel cord stretch at rest, during ambulation, pedicure, and before, during, or after medical treatment.

1 Claim, 14 Drawing Sheets

(56) References Cited

U.S. PATENT DOCUMENTS

| | | | |
|---|---|---|---|
| 4,644,940 A | | 2/1987 | Nakamura |
| 4,813,162 A | * | 3/1989 | Harris ............................... 36/88 |
| 4,819,644 A | | 4/1989 | Cherniak |
| 5,453,083 A | * | 9/1995 | Kasahara ........................ 602/30 |
| 5,802,737 A | | 9/1998 | Beppu |
| 5,870,837 A | | 2/1999 | Poulos |
| 6,093,163 A | | 7/2000 | Chong et al. |
| 6,151,801 A | | 11/2000 | Frederiksen et al. |
| 6,629,943 B1 | * | 10/2003 | Schroder ........................ 602/30 |
| 6,964,645 B1 | | 11/2005 | Smits |
| 7,131,939 B2 | | 11/2006 | Ferri |
| 7,596,887 B2 | | 10/2009 | McClellan |
| 7,794,417 B1 | * | 9/2010 | Zimmerman ................... 602/23 |
| 8,413,349 B2 | * | 4/2013 | Krauss .............................. 36/94 |
| 8,832,971 B2 | * | 9/2014 | Heid .................... A43B 1/0081 36/11.5 |
| 9,173,449 B2 | * | 11/2015 | Heid .................... A43B 1/0081 |
| 2008/0052966 A1 | * | 3/2008 | Pan ................................. 36/3 B |

* cited by examiner

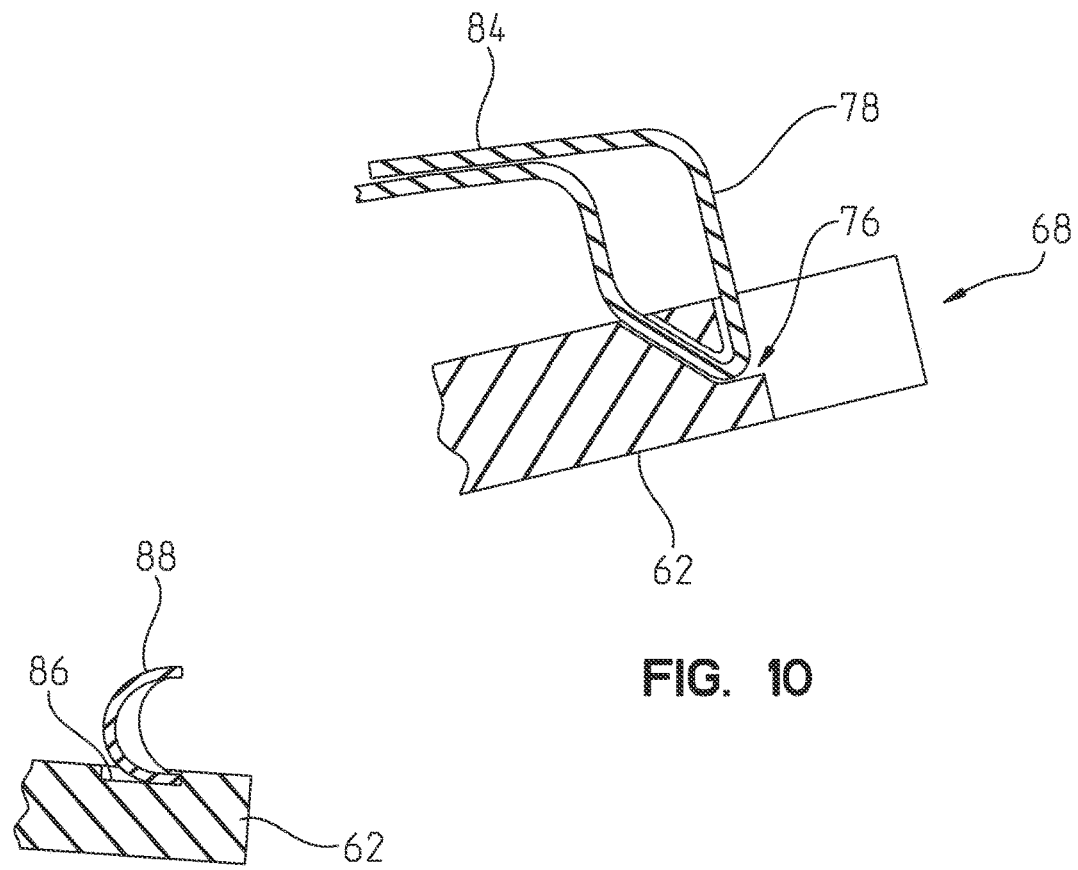
FIG. 10
FIG. 11
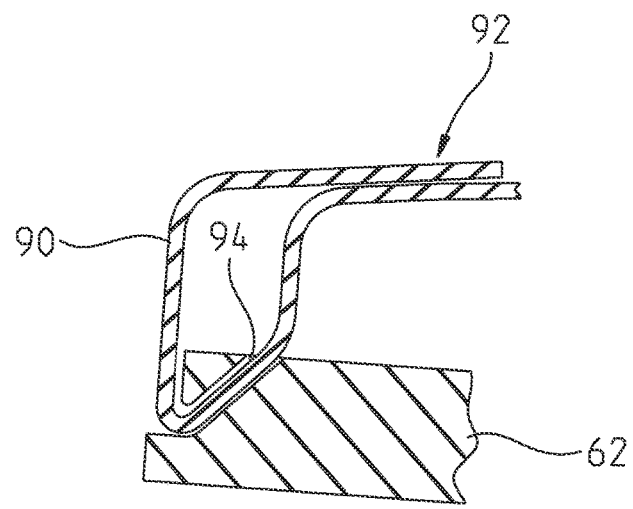
FIG. 12

THERAPEUTIC FOOTWEAR

CROSS-REFERENCE TO RELATED APPLICATIONS

This application is a continuation of U.S. patent application Ser. No. 14/485,949, filed Sep. 15, 2014, which is a continuation of U.S. patent application Ser. No. 13/079,009, filed Apr. 3, 2011, issuing as U.S. Pat. No. 8,832,971 on Sep. 16, 2014, which is a continuation-in-part application of U.S. patent application Ser. No. 11/935,380, filed on Nov. 5, 2007, abandoned, the disclosures of which are expressly incorporated by reference herein.

BACKGROUND AND SUMMARY OF THE INVENTION

Foot pain, bunions, stiff Achilles tendons/heel cords, and plantar fasciitis have long been problems suffered by many, especially women and most especially women who wear high heels. Inherent in high heels is the problem of tight heel cords due to the heel being elevated above the forefoot thus placing the heel cords in a shortened position. Also problematic in this type of footwear is the forward force placed on the foot, from heel to toes, thereby increasing the pressure on the forefoot and the metatarsal heads while forcing the metatarsal-phalangeal joints into an unnaturally increased dorsiflexed and adducted position. Additionally, many high heeled shoes are designed with an ever narrowing toe box which often tapers to a point thus diminishing any normal physiological space between the toes and causing the great toe to deviate laterally. With frequent use of this type of footwear come the aforementioned problems. These problems can also be caused by a number of other factors not limited to a pronated foot, genetics, lifestyle, and activity type and level.

There are many products available to effect a separation between the toes (inserts, braces, and other accessories,) however none of these products incorporates these features contiguously into a footwear for daily wear. Use of any of aforementioned accessories can be labor intensive in applying the device to the toes, foot, or shoe. They may be uncomfortable or impossible to fit into a specific type of shoe as well as unattractive as evidenced by the bunion brace being visible when worn with several shoe styles. Treatments also exist to address pain associated with the above conditions including physical therapy, medication via injection or by mouth, and cryotherapy. Surgery has also been employed to correct the misalignment of the great toe. The present disclosure addresses the root cause of bunion pain, relieving pain without the complications and side effects of surgical intervention.

One embodiment of the present disclosure includes a therapeutic footwear for supporting a wearer's foot having a heel portion, an arch portion, and a plurality of toes including a great toe, the footwear including a horizontally extending base having first and second spaced apart ends, the first end adapted to support the heel portion of the wearer's foot, the second end adapted to support the plurality of toes, and an adjustable strap including an adjustment mechanism and first and second portions, the first portion coupled to the second end of the base and adapted to secure the great toe, the second portion adapted to secure the adjustable strap to the base, the adjustment mechanism adapted to pull the great toe away from the other toes of the plurality of toes.

Another embodiment of the present disclosure includes a therapeutic footwear for supporting a wearer's foot having a heel portion, an arch portion, and a plurality of toes including a great toe, the footwear including a horizontally extending base having first and second spaced apart ends, a passage, a recessed area, and a slot, the first end adapted to support the heel portion of the wearer's foot, the second end adapted to support the plurality of toes, the passage extending laterally through the base, the recessed area positioned on the second end of the base, the slot including a first opening on an upper side of the base and second opening on lateral side of the base, an adjustable strap including an adjustment mechanism and first and second portions, the first portion coupled to the recessed area of the second end of the base and adapted to secure the great toe, the second portion extending through the slot to secure the adjustable strap to the base, the adjustment mechanism adapted to pull the great toe away from the other toes of the plurality of toes, and a second strap coupled to the second portion of the adjustable strap and the second portion of the base, the second strap including a plurality of leaders on a first end and an adjustable portion on a second end, the second end extending around the adjustable strap to secure the second strap around the heel portion, the plurality of leaders coupled to the second portion of the base, Yet another embodiment of the present disclosure includes a footwear insert for providing therapeutic support to a wearer's toes inside the wearer's conventional shoe, the footwear insert including a horizontally extending base having a heel end and a toe end, the base extending horizontally within the conventional shoe, and a band coupled to the toe end of the base, the band adapted to apply a laterally inward pressure to a great toe of the wearer's toes.

A further embodiment of the present disclosure includes a therapeutic footwear for supporting a wearer's foot having a heel portion and plurality of toes including a great toe, the footwear including a horizontally extending base having first and second spaced apart ends, the first end adapted to support the heel portion of the wearer's foot, the second end adapted to support the plurality of toes, an ankle support strap adapted to secure the footwear to the wearer's foot, a first adjustable strap adapted to apply a medial force on the great toe, the first adjustable strap including an adjustment mechanism and first and second portions, the first portion coupled to the second end of the base, the second portion adapted to secure the adjustable strap to the base, the adjustment mechanism adapted to vary the medial force applied to the great toe, and a second adjustable strap adapted to apply a lateral force to a great toe joint, the second adjustable strap including an adjustment mechanism and first and second ends, the first end coupled to the second end of the base, the second end adapted to secure the second adjustable strap to the base, and the adjustment mechanism adapted to vary the lateral force applied to the great toe joint.

Another embodiment of a therapeutic footwear includes a therapeutic footwear for supporting a wearer's foot having a heel portion, an arch portion, and a plurality of toes including a great toe and a great toe joint, the footwear including a horizontally extending base having first and second spaced apart ends, a first and second passage, a first and second recessed area, and a first and second slot, the first end adapted to support the heel portion of the wearer's foot, the second end adapted to support the plurality of toes, the first passage extending diagonally through the base, the second passage extending laterally through the base, the first slot including a first opening on an upper side of the base and a second opening on lateral side of the base, the second slot including a third opening on the upper side of the base and a fourth opening on a medial side of the base, a first adjustable strap including a first adjustment mechanism and first and second portions, the first portion coupled to the first recessed area of the second end of the base and adapted to secure the great toe, the second portion extending through the first portion and the first slot to secure the first adjustable strap to the base, the first adjustment mechanism adapted to apply a medial force on the great toe, and a second adjustable strap including a second adjustment mechanism, and first and second portions, the first portion coupled to the second recessed area of the second end of the base and adapted to support the great toe joint, the second portion extending through the second passage and second slot to secure the second adjustable strap to the base, the second adjustable mechanism adapted to apply a lateral force on the great toe joint.

BRIEF DESCRIPTION OF THE DRAWINGS

The detailed description of the drawings particularly refers to the accompanying figures in which:

FIG. 10 is a cross-sectional view taken along the width of the therapeutic footwear shown in FIGS. 8 and 9;

FIG. 11 is another cross-sectional view taken along the width of the therapeutic footwear shown in FIGS. 8 and 9;

FIG. 12 is another cross-sectional view taken along the width of the therapeutic footwear shown in FIGS. 8 and 9;

DETAILED DESCRIPTION OF THE DRAWINGS

The embodiments of the invention described herein are not intended to be exhaustive or to limit the invention to the precise forms disclosed. Rather, the embodiments selected for description have been chosen to enable one skilled in the art to practice the invention.

Figure 1:
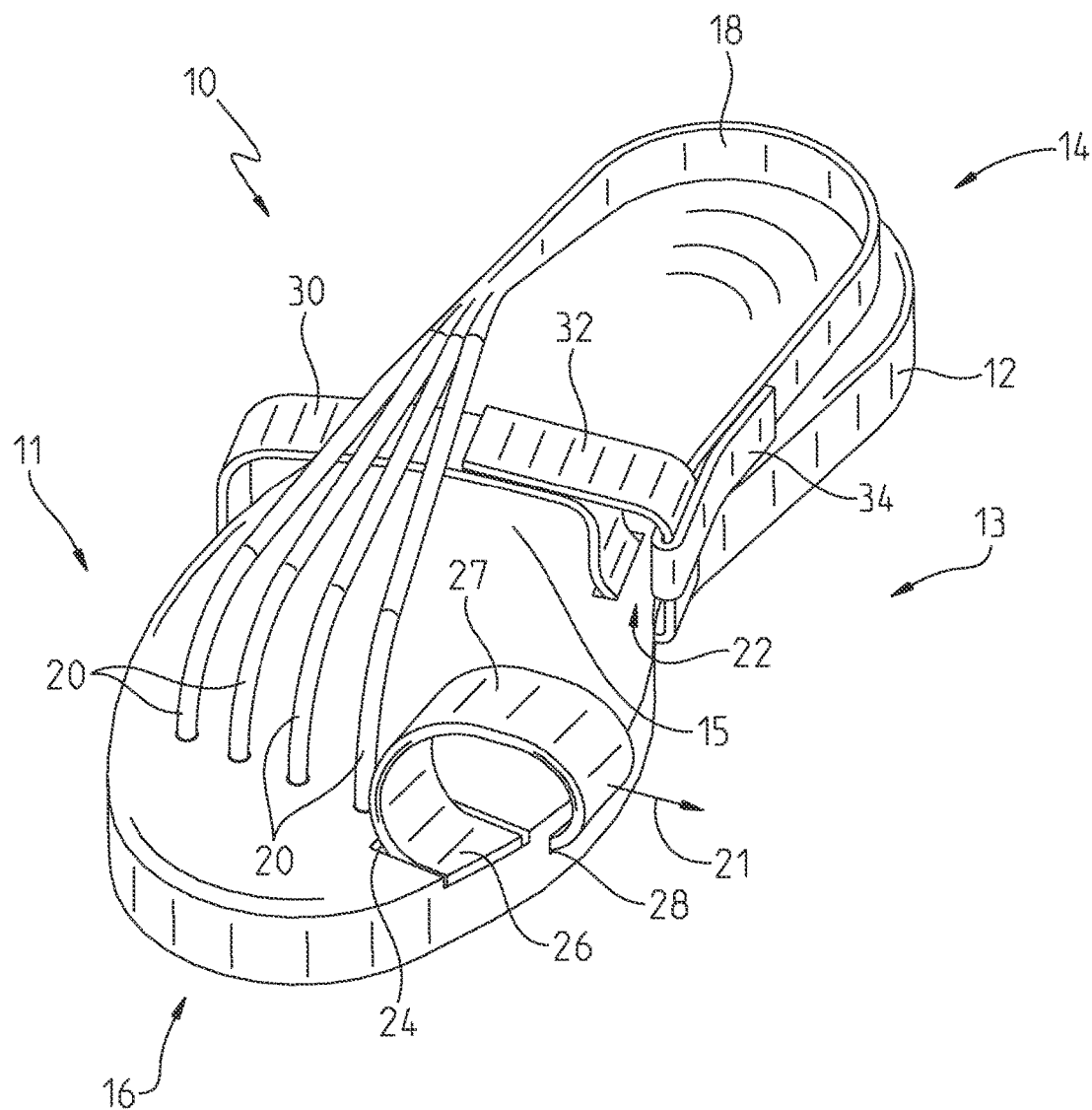
FIG. 1 is a perspective view one embodiment of a therapeutic footwear.
Figure 2:
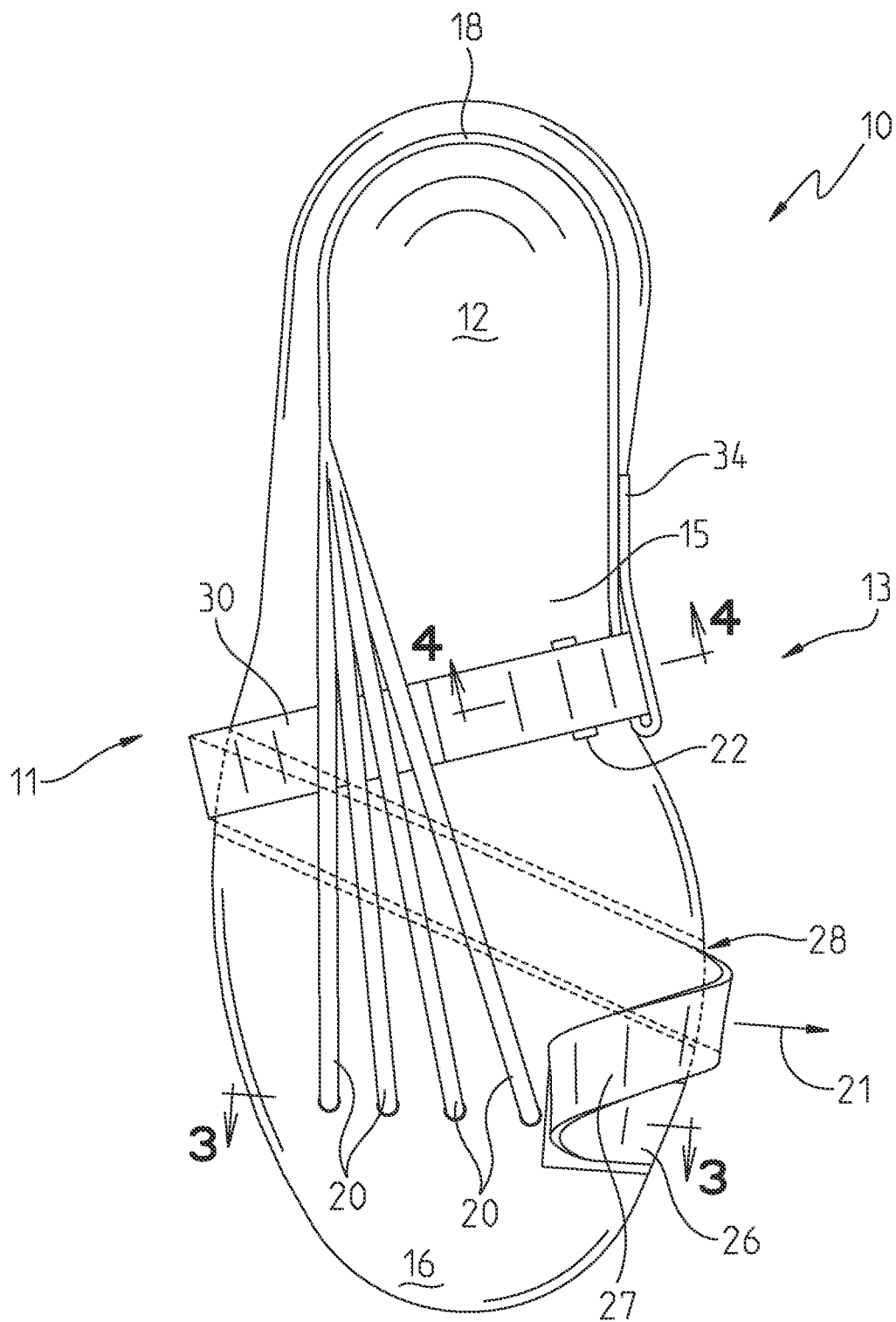
FIG. 2 is a top view of the therapeutic footwear shown in FIG. 1.

Referring to FIGS. 1 and 2, a therapeutic footwear 10 is represented. Footwear 10 is designed to prevent hallux valgus or bunions by maintaining proper great toe alignment and stabilizing the great toe. Footwear 10 also treats existing hallux valgus or bunions and provides pre-surgical and post-bunionectomy/great toe realignment surgery by supporting the great toe, assisting in spreading a wearer's toes, providing support to the wearer's arch to limit excessive pronation, and providing a sustained gentle stretch to the wearer's heel cords, at rest, during ambulation, during pedicure, and before, during, or after medical treatment.

Footwear 10 provides therapeutic relief to the feet of the wearer. Specifically, footwear 10 provides relief for wearers having a bunion on the great toe (commonly referred to as "the big toe" or "first toe"). Footwear 10 may be used to apply a medial force to the great toe of the wearer's foot to force the great toe into the anatomically correct position to relieve bunion pain. For simplicity, footwear 10 is illustrated and explained as only the "right" side shoe or footwear. It should be understood that the "left" side shoe or footwear is a mirror image of footwear 10 shown in FIG. 1.

Figure 4:
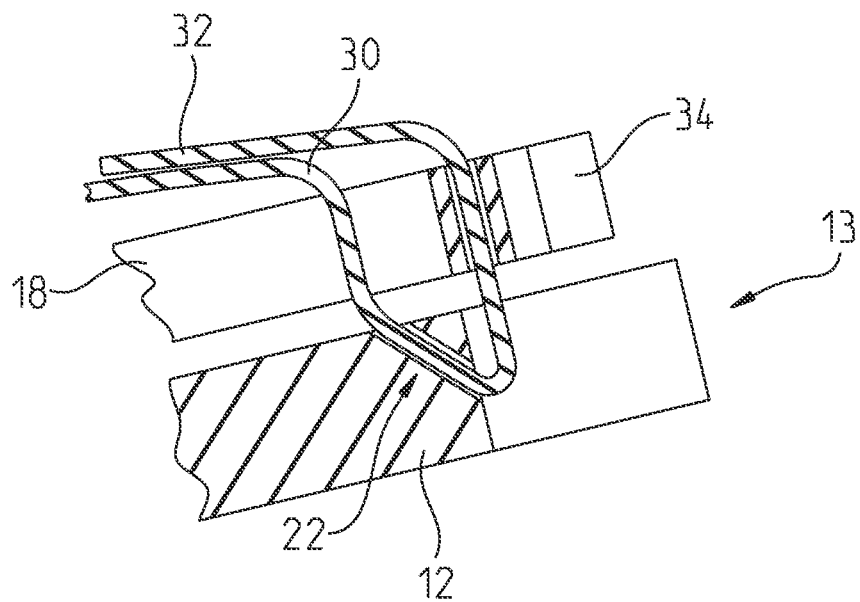
FIG. 4 is a cross-sectional view taken along the length of the therapeutic footwear shown in FIGS. 1 through 3.
Figure 5:
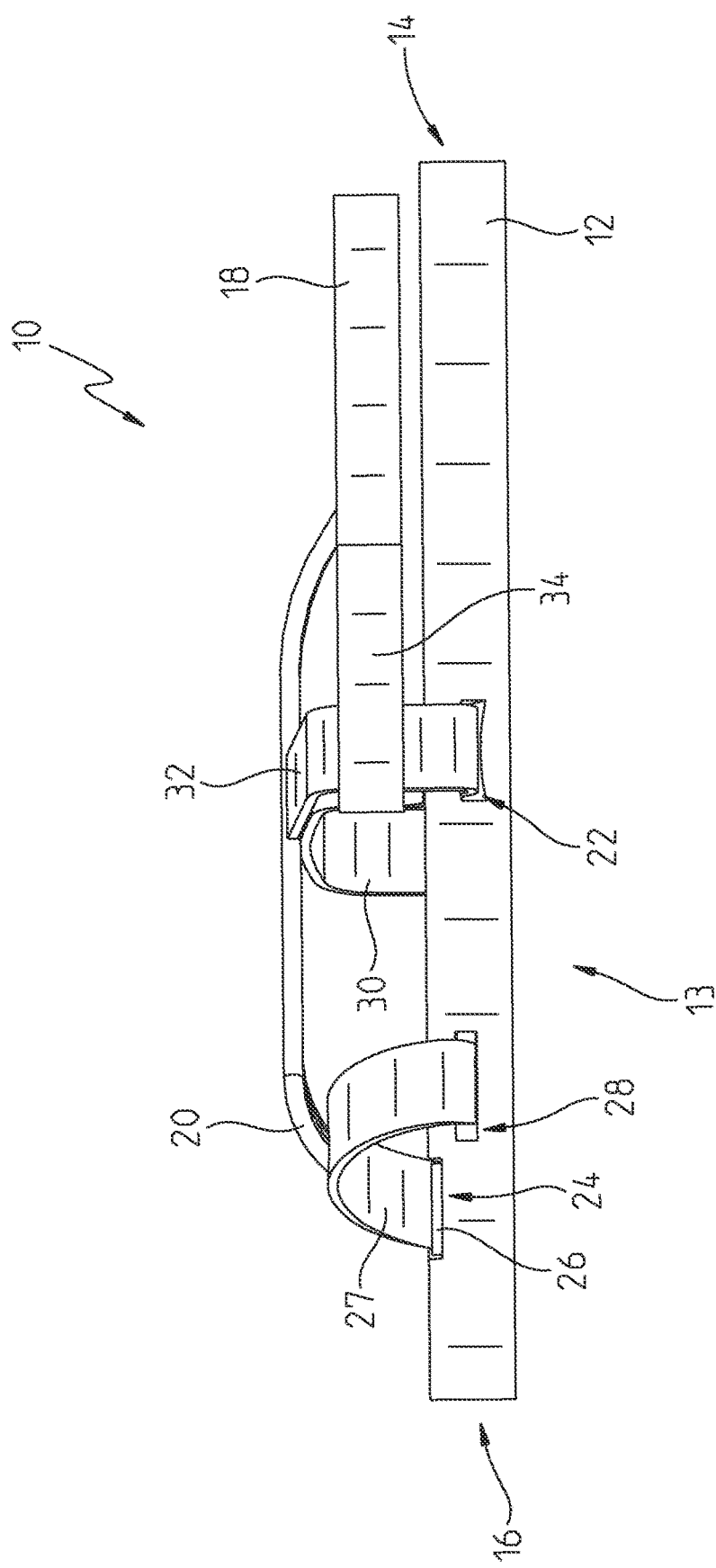
FIG. 5 is a medial side view of the therapeutic footwear shown in FIGS. 1 through 4.

Footwear 10 includes a horizontally extending base 14 having first end 12 and second end 16. Base 14 includes medial side 13 and lateral side 11. First end 12 supports the heel portion of the wearer's foot and second end 16 supports the wearer's toes. The arch of the wearer's foot is supported by section 15 of base 12. Base 12 also includes passage 28 and slot 22. Passage 28 extends diagonally through the interior of base 12 from medial side 12 to lateral side 11. Passage 28 is formed to accept adjustable strap 30. Slot 22, shown in FIG. 4, has a first opening on the upper surface of base 12 and a second opening on medial side 13 of base 12. Slot 22 is also formed to accept strap 30.

Adjustable strap 30 includes first end 26 and second end 32. First end 26 of strap 20 is coupled to recessed area 24 of base 12. When the wearer's foot enters footwear 10, the great toe slides into loop 27 which is formed by strap 30. Strap 30 passes from medial side 13 of base 12 through passage 28 and exits passage 28 on lateral side 11 of base 12. Strap 30 then extends upward and over the top of the wearer's foot (not shown) and extends downward through the first opening of slot 22 in the upper surface of base 12. Strap 30 exits slot 22 through the second opening on medial side 13 of base 12.

The wearer may adjust medial force 21 on the great toe by adjusting an adjustment mechanism on adjustable strap 30. In the illustrative embodiment, second end 32 of adjustable strap 30 includes Velcro and couples to a corresponding Velcro surface on the upper surface of strap 30 over the top of the wearer's foot. Adjustable strap 30 may include any suitable adjustment mechanism such as Velcro, snaps, pins, or buckles. To apply more medial force on the great toe, second end 32 of adjustable strap 30 is tightened by pulling it toward lateral side 11 of base 12 and secured by the adjustment mechanism of adjustable strap 30. Conversely, to lessen medial pressure 21 on the great toe, second end 32 of adjustable strap 30 is loosened to allow it to move toward medial side 13 of base 12 until it is secured by the adjustment mechanism of adjustable strap 30.

Figure 3:
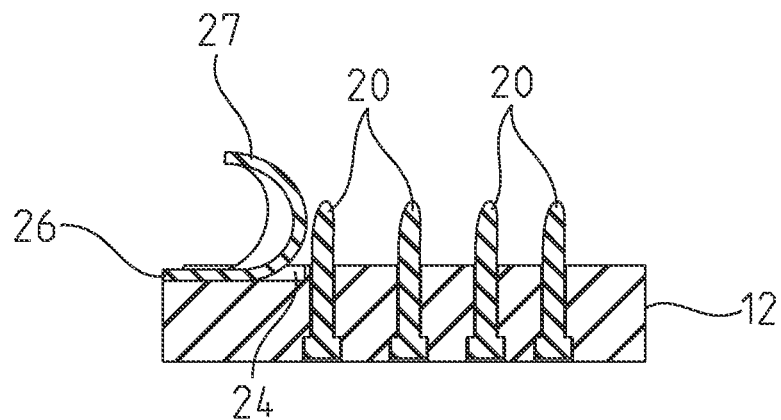
FIG. 3 is a cross-sectional view taken along the front of the therapeutic footwear shown in FIGS. 1 and 2.

Footwear 10 also includes second strap 18 to secure footwear 10 to the wearer's heel portion. Second strap 18 includes first end 34 which is looped around adjustable strap 30 on medial side 13 of base 12 in the illustrative embodiment. Second strap 18 also includes plurality of leaders 20 which couple to second end 16 of base 12, shown in FIG. 3. Leaders 20 are coupled to base 12 at positions corresponding to the spacing between the wearer's toes to separate the wearer's toes when the foot is inserted into footwear 10. In other embodiments, leaders 20 may be replaced by a strap connected only to loop 27 of adjustable strap 30.

Second strap 18 may include an adjustment mechanism similar to adjustable strap 30. In the illustrative embodiment, first end 32 includes a Velcro surface corresponding to a second Velcro surface on second strap 18. In the illustrative embodiment shown in FIGS. 1 and 2, the wearer may secure footwear 10 to the foot by pulling first end 34 through the loop formed by adjustable strap 30 and securing the opposing Velcro surfaces on second strap 18. As discussed above, the adjustment mechanism of second strap 18 may be any suitable fastening system including Velcro, snaps, pins, or buckles.

The components of footwear 10 may be formed from leather, rubber, synthetic material, cloth, sheepskin, canvas, polyester, polyurethane, nylon, polypropylene, neoprene, mesh, recycled materials, plastic, or any other suitable material. Additionally, straps 18 and 30 may be formed from any suitable elastic or inelastic materials such as nylon, cloth, leather, plastic, rubber, polyester, or canvas.

Figure 6:
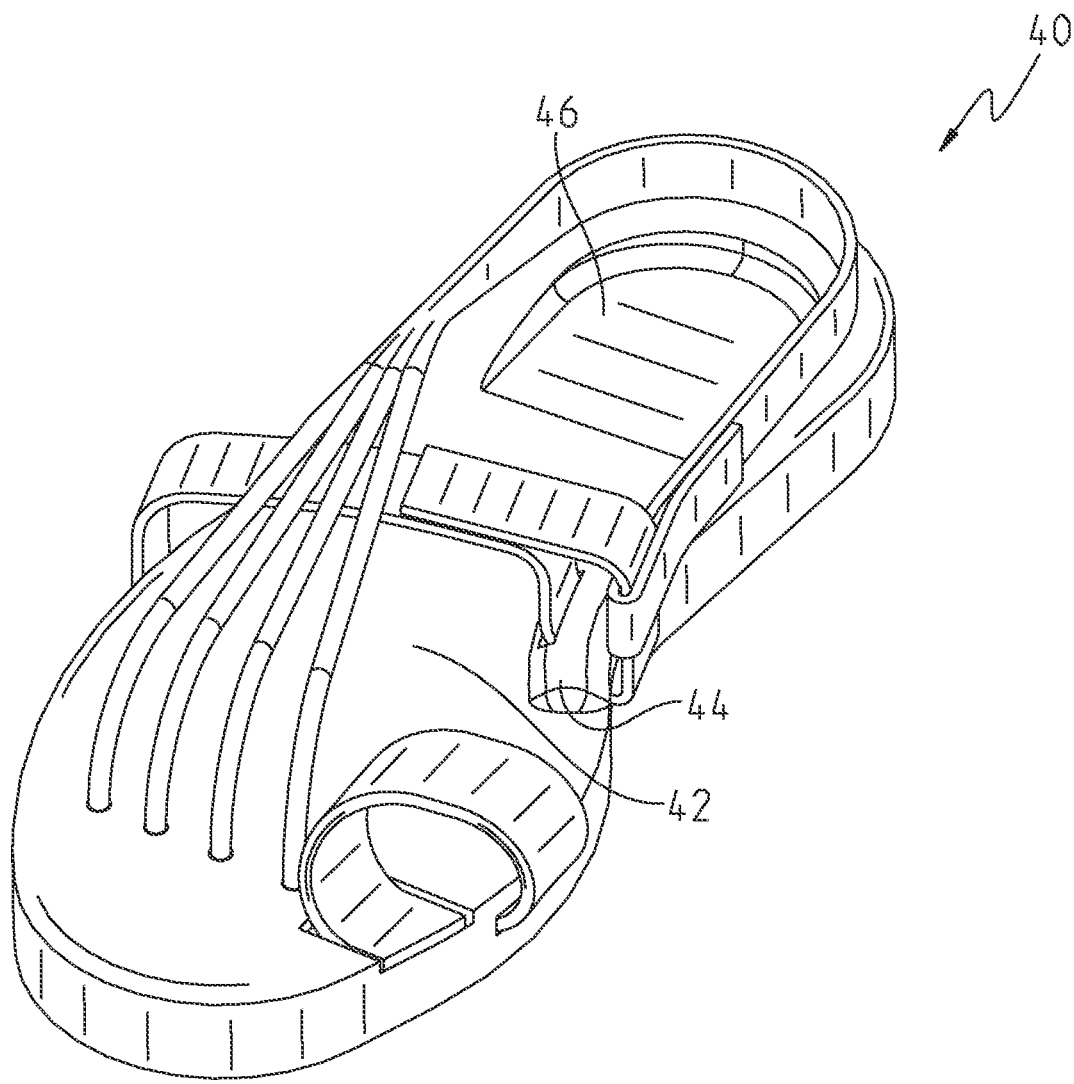
FIG. 6 is a perspective view of another embodiment of a therapeutic footwear.

Another embodiment of a therapeutic footwear is shown in FIG. 6. Therapeutic footwear 40 is similar to therapeutic footwear 10 shown above with several exceptions. Horizontally extending base 42 of footwear 40 includes recessed area 46 below the wearer's heel portion. Recessed area 46 creates a "negative heel" which may provide a gentle calf stretch. Additionally recessed area 46 may provide relief to the toes of the wearer by reducing the downward and forward pressure of the wearer's body on the tarsal joints, especially after a period of wearing shoes have a positive heel, i.e. high heeled shoes. Therapeutic footwear 40 may also include arch support 44 formed within or coupled to base 42. Arch support 44 may be formed to any suitable height or width to provide arch support and pain relief to the wearer's arch.

Figure 7:
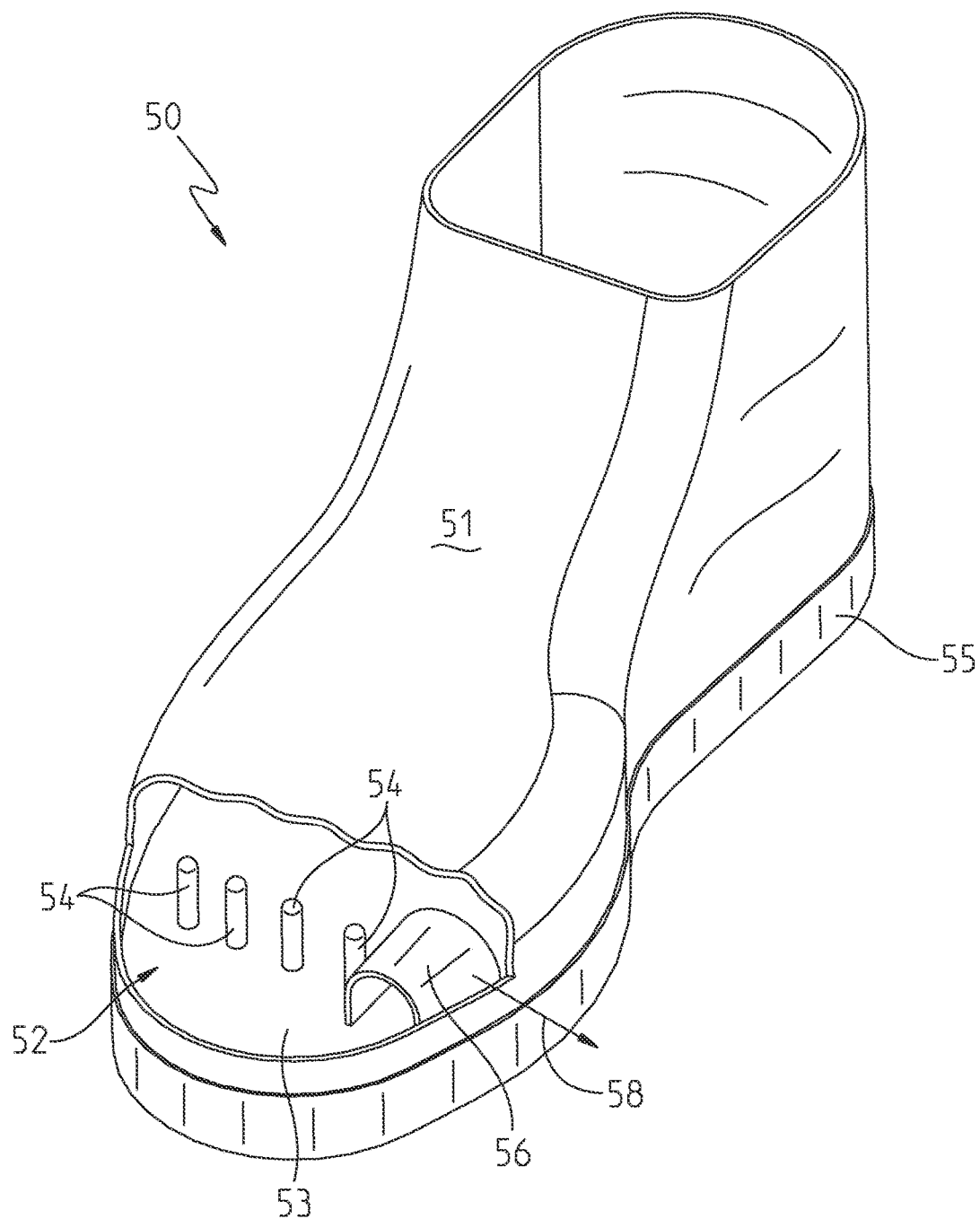
FIG. 7 is a perspective view of a conventional shoe having therapeutic features.

One embodiment of a conventional shoe having therapeutic features is shown in FIG. 7. A conventional shoe or footwear 50 is shown including sole 55 and covering surface 51. Examples of conventional shoes may include boots, tennis shoes, loafers, slippers, moccasins, clogs, or any other suitable closed toe or semi-closed toe shoe. Therapeutic portion 52 is shown within conventional shoe 50. Therapeutic portion 52 includes base 53, extensions 54, and band 56. Base 53 extends the entire length of the interior cavity of shoe 50 and may be formed of a rigid or flexible material. Extensions 54 are positioned to separate the wearer's toes when the foot is inserted into shoe 50. When the foot is inserted into shoe 50, the great toe enters band 50 which applies medial force 58 to pull the great toe toward the center line of the wearer's body to relieve bunion pain. Band 56 may be formed from an elastic or inelastic material. In other embodiment, extensions 54 may be absent.

In another embodiment, similar to footwear 50, therapeutic portion 52 may be formed as an insert incorporating extensions 54 and band 56 of therapeutic portion 52, as shown in FIG. 7. In this embodiment, band 56 may include an adjustment means such as a Velcro portion to allow the wearer to vary medial force 58 on the great toe. The adjustment means may include a corresponding Velcro portion positioned on the bottom side of the insert to couple to the Velcro portion affixed to band 56. The adjustment means may include any other suitable fastener such as buckles or buttons.

Figure 8:
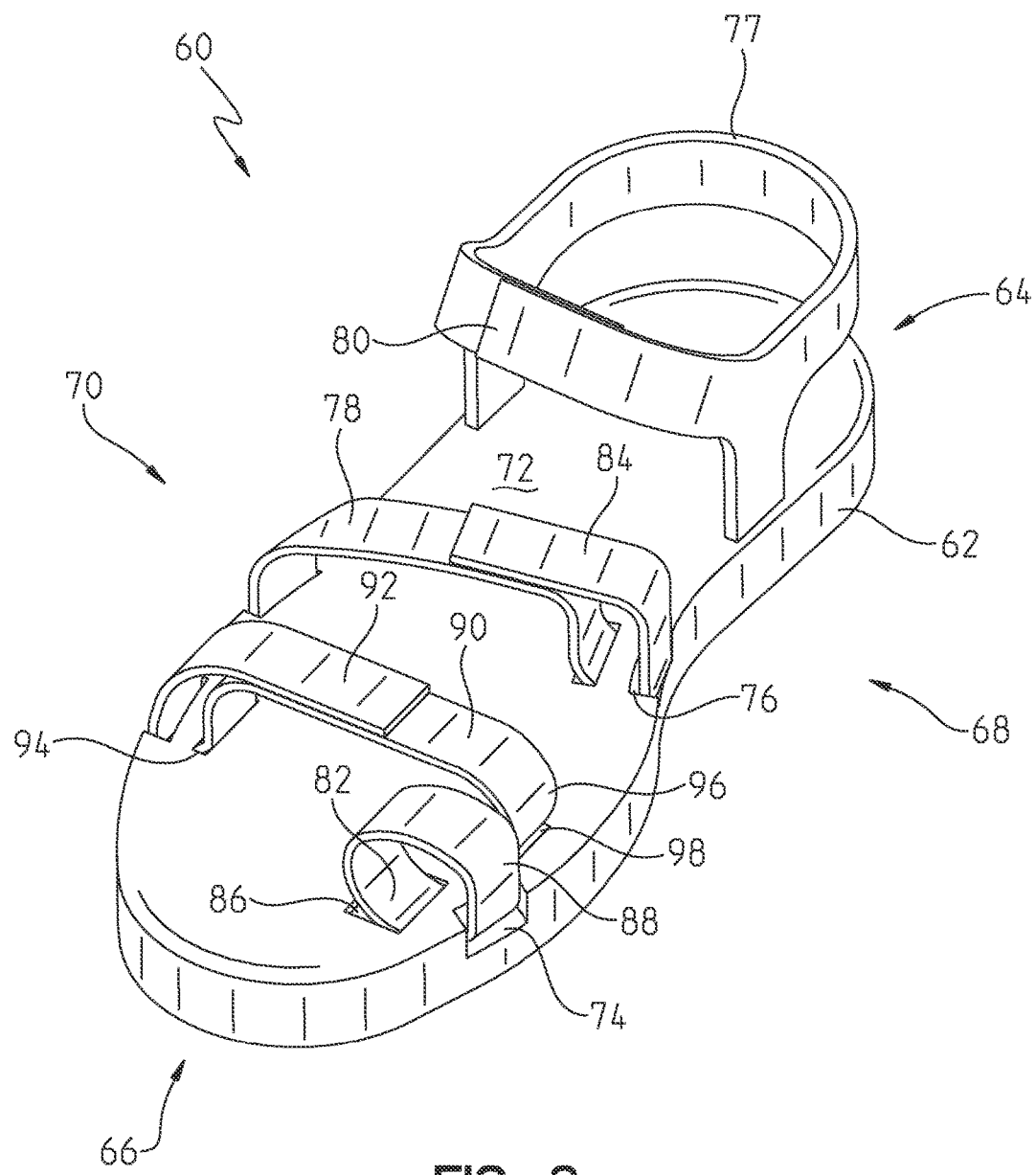
FIG. 8 is a perspective view of another embodiment of a therapeutic footwear.
Figure 9:
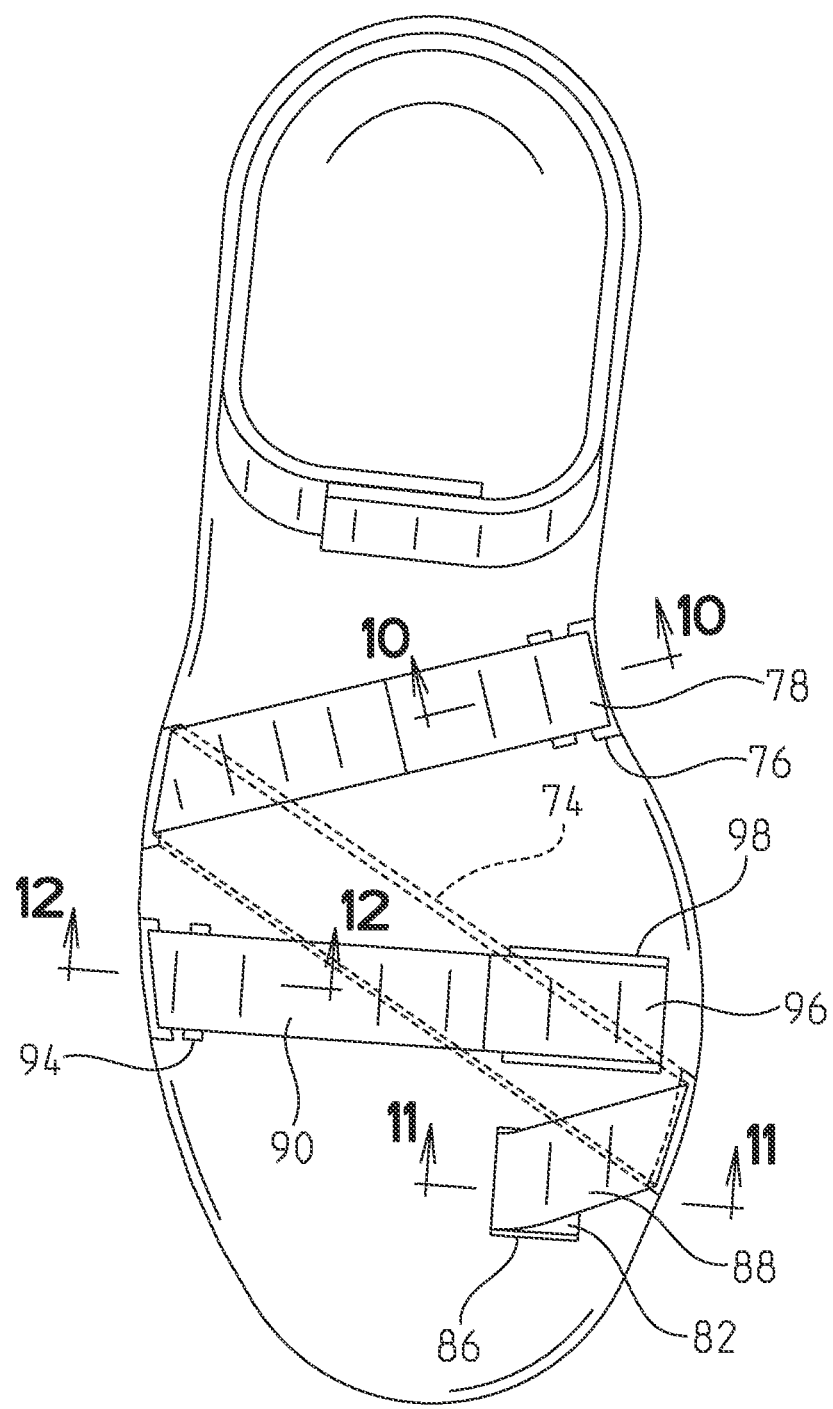
FIG. 9 is a top view of the therapeutic footwear shown in FIG. 8.

Another embodiment of a therapeutic footwear is shown in FIG. 8. Footwear 60 includes horizontally extending base 62 having first end 64 and second end 66. Base 62 includes medial side 68 and lateral side 70. First end 64 supports the heel portion of the wearer's foot and second end 66 supports the wearer's toes. The arch of the wearer's foot is supported by section 72 of base 60. Base 62 also includes passage 74 and slot 76, shown in FIG. 9. Passage 74 extends diagonally through the interior of base 62 from medial side 68 to lateral side 70. Passage 74 is formed to accept adjustable strap 78. Slot 76, shown in FIGS. 8 and 10, has a first opening on the upper surface of base 62 and a second opening on medial side 68 of base 62. Slot 76 is also formed to accept strap 78.

Adjustable strap 78 includes first end 82 and second end 84. First end 82 of strap 78 is coupled to recessed area 86, shown in FIG. 11, on second end 66 of base 62. When the wearer's foot enters footwear 60, the great toe slides into loop 88 which is formed by strap 78. Strap 78 passes from medial side 68 of base 62 through passage 74 and exits passage 74 on lateral side 70 of base 62. Strap 78 then extends upward and over the top of the wearer's foot, shown in FIG. 14, and extends downward through the first opening of slot 76 in the upper surface of base 62. Strap 78 exits slot 76 through the second opening on medial side 68 of base 62. In the illustrative embodiment, second end 84 of adjustable strap 78 includes hook and loop style material and couples to a corresponding surface on the upper surface of strap 78 over the top of the wearer's foot. Adjustable strap 78 may include any suitable adjustment mechanism such as snaps, pins, or buckles.

Footwear 60 also includes an ankle support strap 77 to secure footwear 60 to the wearer's heel portion or ankle. Ankle support strap 77 includes adjuster 80 which allows the wearer to adjust ankle support strap 77. In the illustrative embodiment, adjuster 80 includes overlapping hook and loop style material on the ends of ankle support strap 77. Adjuster 80 may include any suitable adjustment mechanism such as snaps, pins, or buckles.

Footwear 60 also includes second adjustable strap 90 having first end 96 and second end 92. First end 96 of second adjustable strap 90 is coupled to recessed area 98 of base 62. Second end 92 extends over the wearer's foot and extends downward through the first opening of slot 94 in the upper surface of base 62. Strap 90 exits slot 94 through the second opening on lateral side 70 of base 62. In the illustrative embodiment, second end 92 of adjustable strap 90 includes hook and loop style material and couples to a corresponding surface on the upper surface of strap 90 over the top of the wearer's foot. Second adjustable strap 90 may include any suitable adjustment mechanism such as snaps, pins, or buckles.

Figure 14:
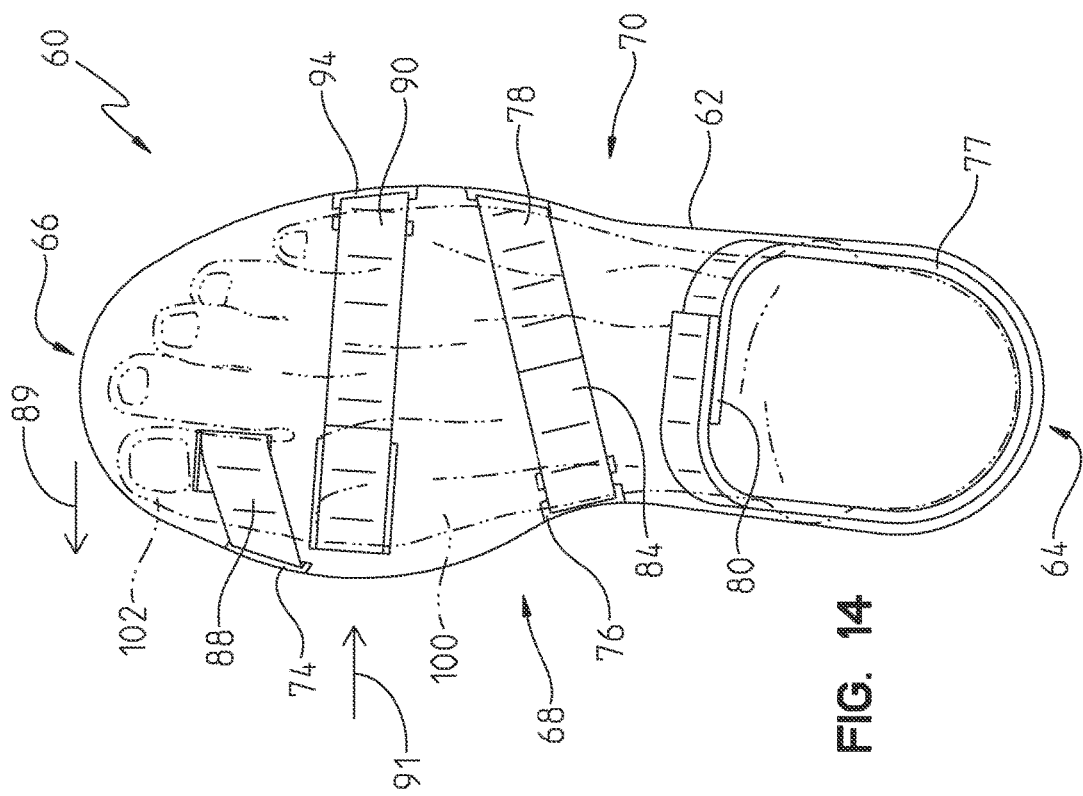
FIG. 14 is a top view of a wearer's foot shown the therapeutic footwear shown in FIGS. 8-13.
Figure 13:
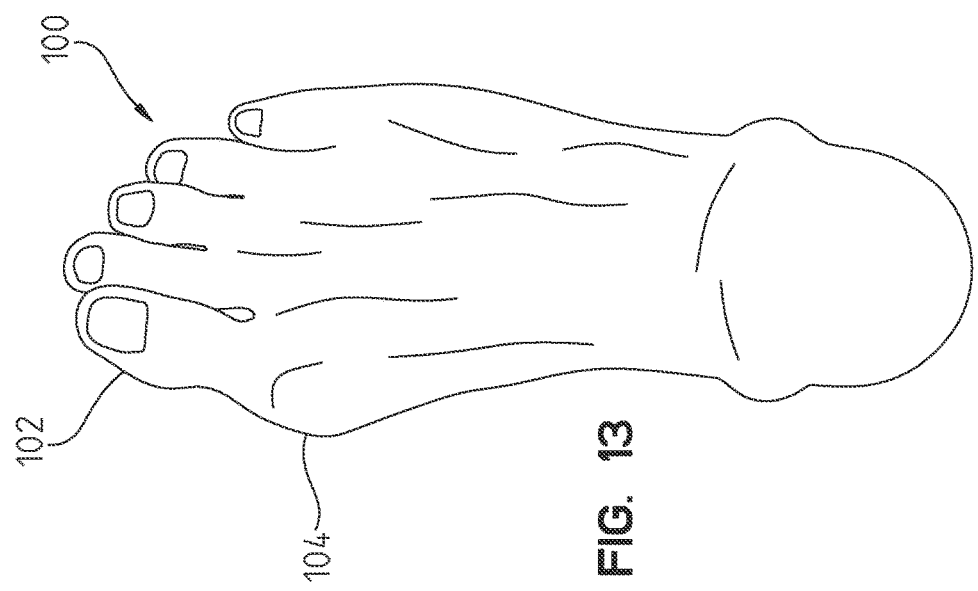
FIG. 13 is a top view of a wearer's foot.

FIG. 13 illustrates wearer's foot 100 having displaced great toe 102 and a first metatarsal-phalangeal joint, commonly referred to as the great toe joint 104. In the illustrative example, great toe 102 is displaced laterally forming a bunion on great toe joint 104. FIG. 14 illustrates wearer's foot 100 inserted into therapeutic footwear 60. The wearer may adjust medial force 89 on great toe 102 by adjusting the tension of adjustable strap 78. For example, to increase medial force 89 on great toe 102, second end 84 of adjustable strap 78 is tightened by pulling it toward lateral side 70 of base 62 and secured by the adjustment mechanism of adjustable strap 78. Conversely, to lessen medial force 89 on the great toe, second end 84 of adjustable strap 78 is loosened to allow it to move toward medial side 68 of base 62 until it is secured by the adjustment mechanism of adjustable strap 78. Second adjustable strap 90 applies lateral force 91 to great toe joint 104. The wearer may adjust lateral force 91 on great toe joint 104 by adjusting the tension of second adjustable strap 90. Medial force 89 on great toe 102 and lateral force 91 on great toe joint 104 work together to straighten toe 102. When the tension of adjustable straps 78 and 90 are adjusted correctly, great toe 102 is moved from its displaced position, shown in FIG. 13, to its anatomically correct position as shown in FIG. 14. Use of therapeutic footwear 60 may lessen or relieve toe or foot pain by maintain great toe 102 in an anatomically correct position.

The components of footwear 60 may be formed from leather, rubber, synthetic material, cloth, sheepskin, canvas, polyester, polyurethane, nylon, polypropylene, neoprene, mesh, recycled materials, plastic, or any other suitable material. Additionally, all straps may be formed from any suitable elastic or inelastic materials such as nylon, cloth, leather, plastic, rubber, polyester, or canvas.

Figure 15:
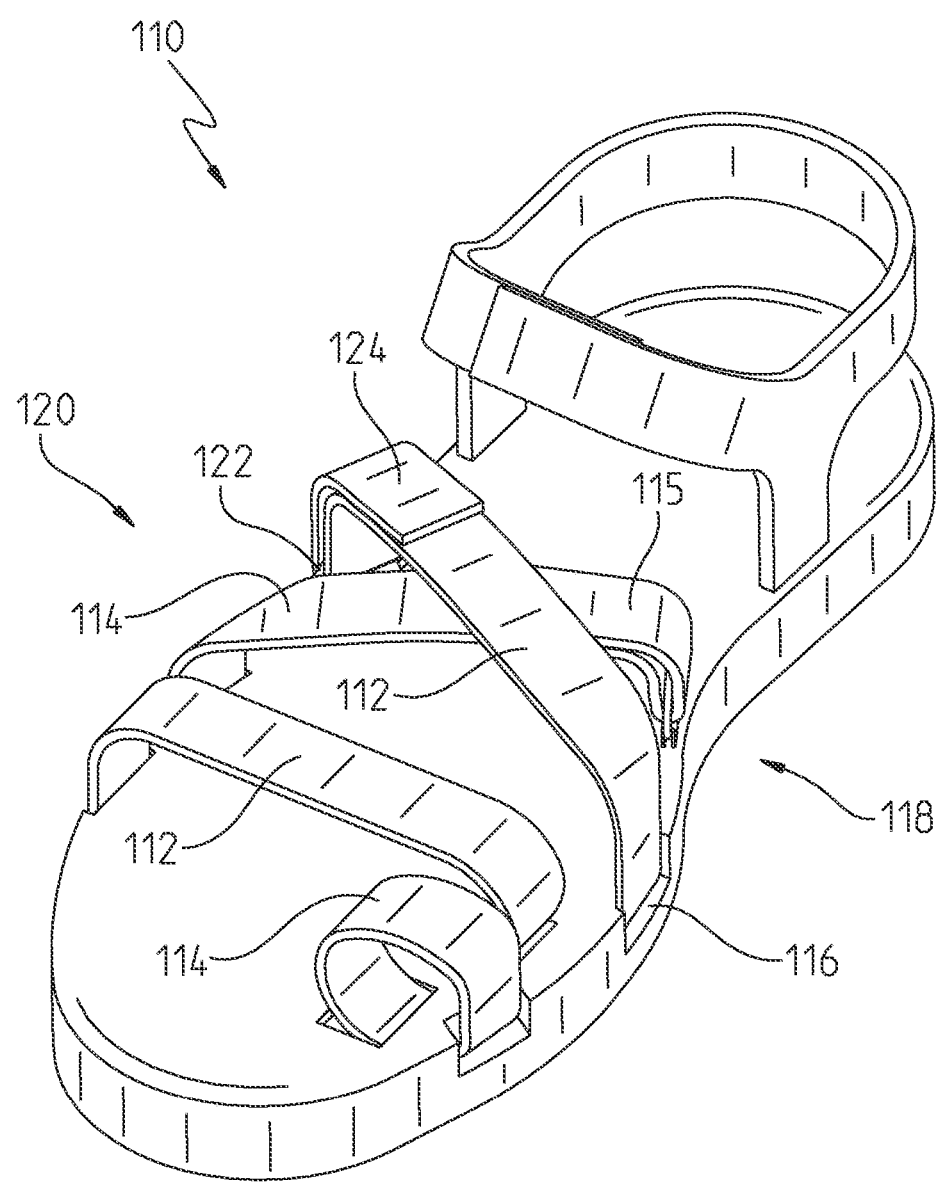
FIG. 15 is a perspective view of another embodiment of a therapeutic footwear.
Figure 16:
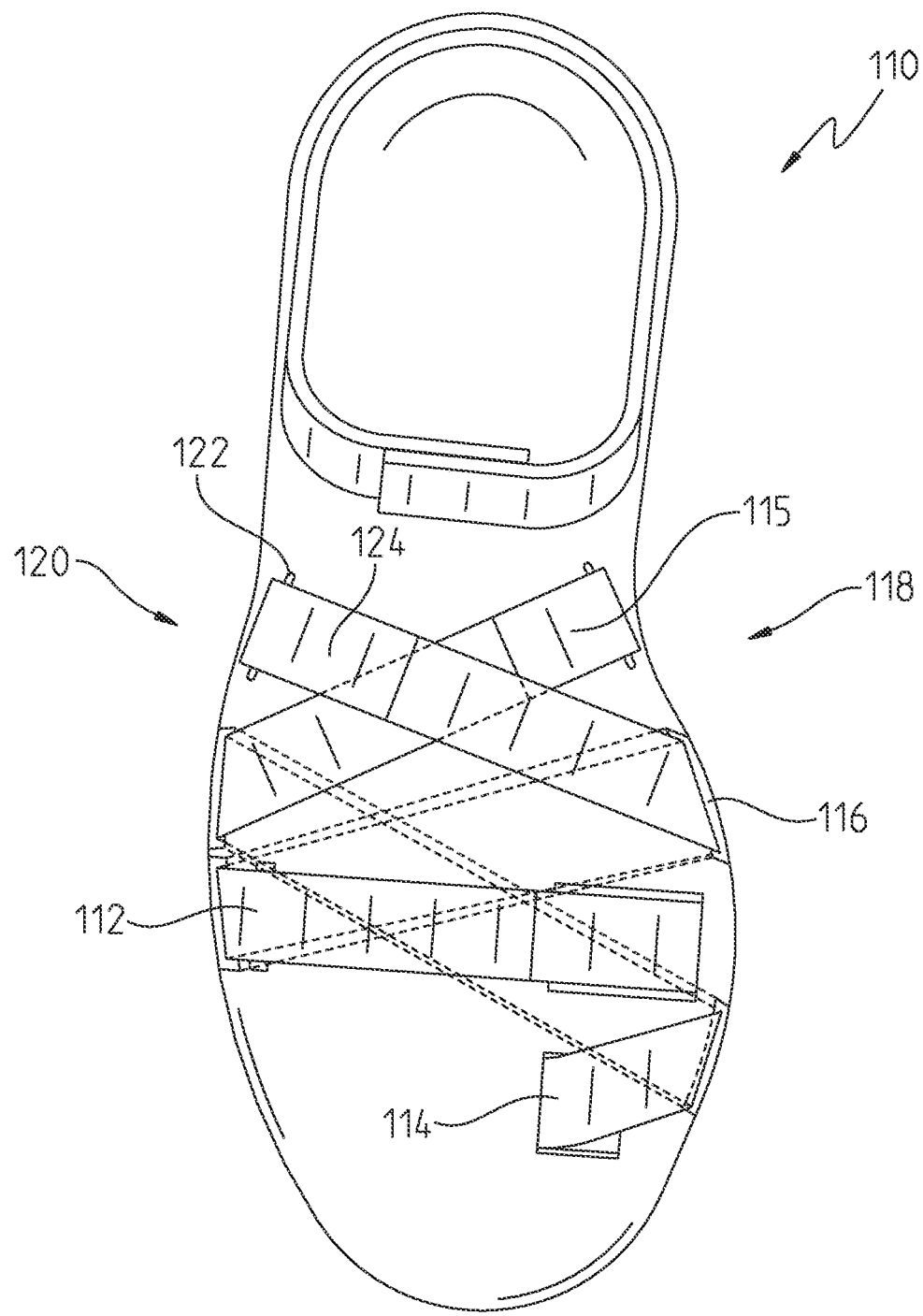
FIG. 16 is a top view of the therapeutic footwear shown in FIG. 15.

Another embodiment of a therapeutic footwear is shown in FIGS. 15 and 16. Therapeutic footwear 110 is similar to footwear 60 shown in FIGS. 8-14 with the exception that adjustable straps 112 and 114 of footwear 110 are oriented in a crossed pattern relative to adjustable straps 90 and 78 of footwear 60. Adjustable strap 114 of footwear 110 is in the same position as adjustable strap 78 of footwear 60 and performs the same function. Second adjustable strap 112 of footwear 110 differs from adjustable strap 90 of footwear 60 in that it extends laterally through channel 116 in footwear 110. Adjustable strap 112 then extends from medial side 118 of footwear 110 to lateral side 120 across the top of the wearer's foot and across the top of adjustable strap 114. Adjustable strap 112 extends through loop 122 and includes adjuster 124. In the illustrative example, adjuster 124 includes hook and loop material to allow the wearer to vary the tension on adjustable strap 112 which applies lateral force on the great toe joint. In an alternative embodiment (not shown), adjustable strap 112 may extend through a slot that replaces loop 122. Additionally, adjuster 124 may include buttons, buckles, snaps, or any other suitable adjustment mechanism. Adjustable strap 114 also includes adjuster 115 which is similar to adjuster 124 and allows the wearer to vary the medial force on the great toe.

Figure 17:
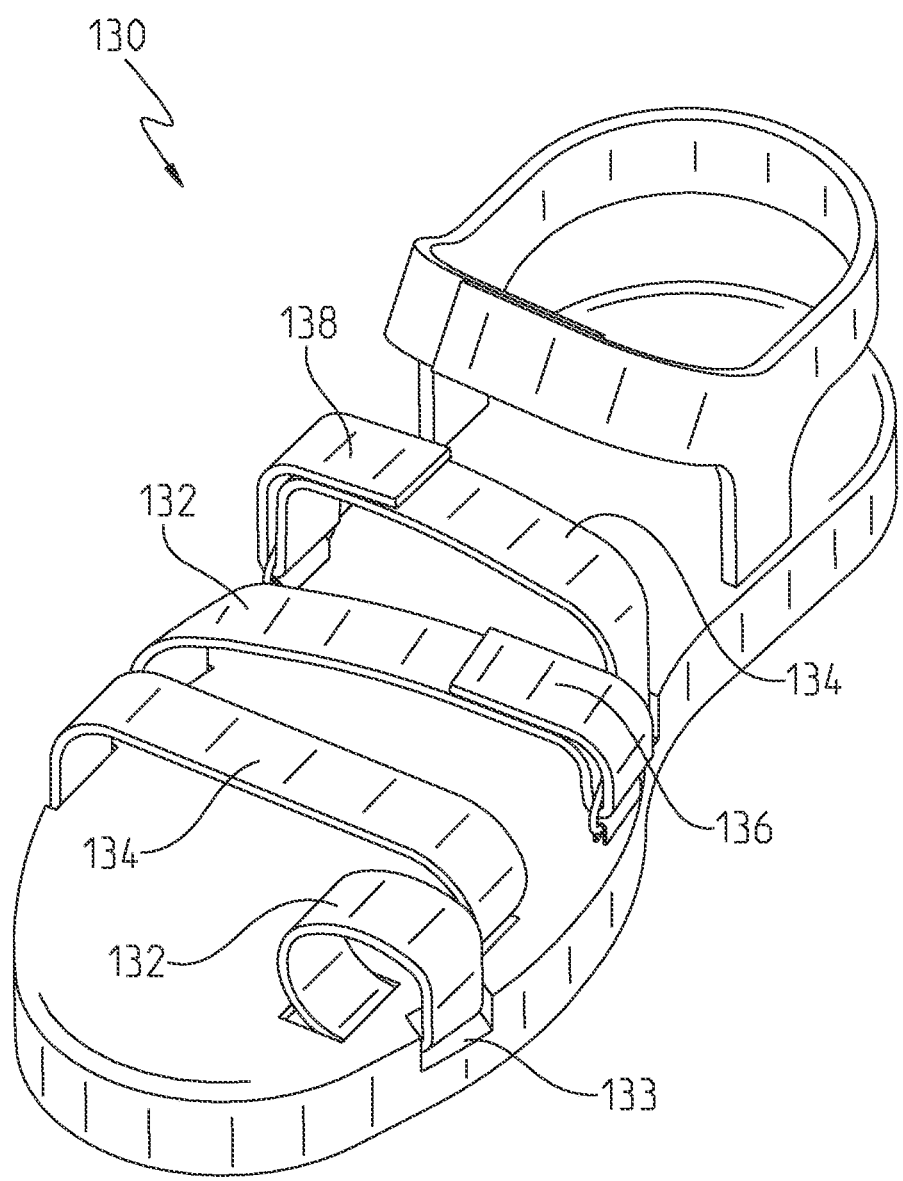
FIG. 17 is a perspective view of another embodiment of a therapeutic footwear.
Figure 18:
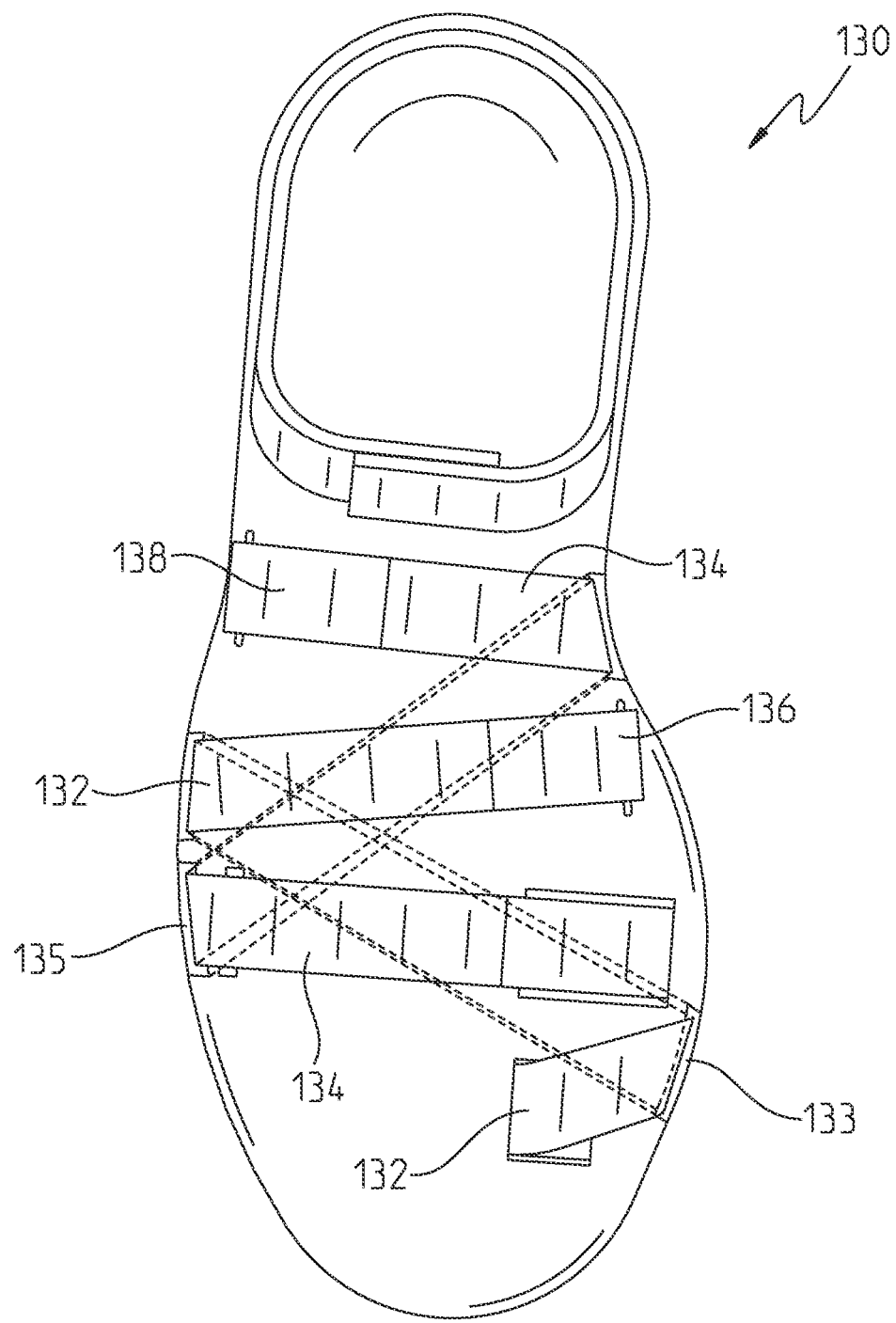
FIG. 18 is a top view of the therapeutic footwear shown in FIG. 15.

Another embodiment of a therapeutic footwear is shown in FIGS. 17 and 18. In this illustrative embodiment, therapeutic footwear 130 includes adjustable straps 132 and 134 which are similar to adjustable straps 112 and 114 of footwear 110 in FIGS. 15 and 16. Adjustable strap 132 extends through channel 133 in footwear 130 and extends over the top of the wearer's foot. Adjuster 136 allows the wearer to vary the medial force applied to the great toe. Adjustable strap 134 extends through channel 135 and extends over the top of the wearer's foot. Adjust 138 allows the wearer to vary the lateral force applied to the great toe joint.

The embodiments shown in FIGS. 15-18 illustrate alternative strapping arrangements that may be used to secure the therapeutic footwear to the wearer's foot and to vary the pressure applied to the great toe and great toe joint. The present disclosure contemplates any therapeutic footwear that allows the wearer to apply opposing forces on the great toe and great toe joint to relieve bunion pain. While the illustrative embodiments only illustrate two adjustable straps and one ankle support strap, any suitable number of straps or mechanisms may be used to attach the therapeutic footwear to the wearer's foot.

Although the invention has been described in detail with reference to certain preferred embodiments, variations and modifications exist within the spirit and scope of the invention as described and defined in the following claims.

The invention claimed is:

1. A therapeutic footwear for supporting a wearer's foot having a heel portion and plurality of toes including a great toe having a great toe joint, the footwear including:
   a horizontally extending base having first and second spaced apart ends, the first end adapted to support the heel portion of the wearer's foot, the second end adapted to support the plurality of toes;
   an ankle support strap adapted to secure the footwear to the wearer's foot;
   a first adjustable strap adapted to apply a medial force on the great toe, the first adjustable strap including an adjustment mechanism and first and second portions, the first portion coupled to the second end of the base, the second portion adapted to secure the adjustable strap to the base, the adjustment mechanism adapted to vary the medial force applied to the great toe, the first adjustable strap forms a loop sized and positioned on a medial side of the base to surround only the great toe of the plurality of toes; and
   a second adjustable strap adapted to apply a lateral force to a great toe joint, the second adjustable strap including an adjustment mechanism and first and second ends, the first end coupled to the second end of the base, the second end adapted to secure the second adjustable strap to the base, and the adjustment mechanism adapted to vary the lateral force applied to the great toe joint.

* * * * *